(12) United States Patent
Janson

(10) Patent No.: US 11,170,974 B2
(45) Date of Patent: Nov. 9, 2021

(54) OBTAINING AN ENERGY SPECTRUM OF A FOCUSED ION BEAM

(71) Applicant: RaySearch Laboratories AB, Stockholm (SE)

(72) Inventor: Martin Janson, Enskededalen (SE)

(73) Assignee: RaySearch Laboratories AB, Stockholm (SE)

(*) Notice: Subject to any disclaimer, the term of this patent is extended or adjusted under 35 U.S.C. 154(b) by 0 days.

(21) Appl. No.: 17/097,199

(22) Filed: Nov. 13, 2020

(65) Prior Publication Data
US 2021/0159047 A1    May 27, 2021

(30) Foreign Application Priority Data

Nov. 21, 2019 (EP) ..................................... 19210528

(51) Int. Cl.
    *H01J 37/30*      (2006.01)
    *H01J 37/05*      (2006.01)
    *H01J 37/304*      (2006.01)

(52) U.S. Cl.
    CPC ............ *H01J 37/304* (2013.01); *H01J 37/05* (2013.01)

(58) Field of Classification Search
    CPC ...... H01J 37/304; H01J 37/05; A61N 5/1075; A61N 5/1031
    See application file for complete search history.

(56) References Cited

U.S. PATENT DOCUMENTS

| | | | |
|---|---|---|---|
| 2017/0304650 A1* | 10/2017 | Inaniwa | A61B 6/025 |
| 2017/0304651 A1* | 10/2017 | Takayanagi | A61N 5/1043 |
| 2018/0243586 A1* | 8/2018 | Ramezanzadeh Moghadam | G16H 20/40 |
| 2018/0256919 A1* | 9/2018 | Shen | A61N 5/1043 |
| 2018/0277278 A1* | 9/2018 | Liu | A61N 5/10 |

* cited by examiner

*Primary Examiner* — Sean M Luck
(74) *Attorney, Agent, or Firm* — Faegre Drinker Biddle & Reath LLP

(57) ABSTRACT

It is provided a method for obtaining an energy spectrum of a focused ion beam when a Bragg peak chamber is used to measure an integrated depth dose, IDD. The method comprises the steps of: simulating doses of a set of nominally mono energetic focused ion beams; determining a lateral extension of a Bragg peak chamber to evaluate; calculating a set of theoretic component IDD curves, CIDDs, by laterally integrating the dose of the simulated set of the nominally mono energetic focused ion beams, over the lateral extension of the Bragg peak chamber; storing calculated CIDDs; obtaining a measured IDD of a focused ion beam with a nominal energy using the Bragg peak chamber; and performing a fit of a linear combination of CIDDs to the measured IDD, to determine an energy spectrum for the focused ion beam with the nominal beam energy.

13 Claims, 4 Drawing Sheets

OBTAINING AN ENERGY SPECTRUM OF A FOCUSED ION BEAM

This application claims the benefit of European Patent Application No. EP19210528.6, filed Nov. 21, 2019, the entire contents of which is incorporated by reference herein.

TECHNICAL FIELD

The present disclosure relates to the field of radiation therapy and in particular to generating radiation therapy plans while restricting to a subset of fluence elements.

BACKGROUND

In ion beam therapy, a beam of ions (e.g. protons or heavier ions, such as carbon ions) is directed towards a target volume. The target volume can e.g. represent a cancer tumour. The ions penetrate the tissue and deliver a dose of energy to destroy cancer cells. An advantage of ion beam therapy is that there is a significant peak in the dose distribution, known as the Bragg peak. The Bragg peak is a peak of dose delivery occurring at a certain depth, after which the dose delivery falls of quickly. This can be compared with electron beam therapy or X-ray therapy where the peak occurs very close to entering the tissue and dose fall off cannot be controlled with the same sharp fall off as for ion therapy.

The depth of the Bragg peak in the patient can be controlled by adjusting an energy amount of the ions. Lateral position can be controlled using electromagnets to deflect the beam. A spot in ion beam therapy refers to a collection of ions of a specific energy level at a specific lateral location. The number of particles delivered to a spot is commonly referred to as the spot weight. By providing doses in spots in many different locations in a three-dimensional space, the target volume can be covered with a desired dose distribution. This procedure is called active scanning ion beam therapy, also known as pencil beam scanning.

The planning of how the spots should be delivered is performed in a treatment planning system. The treatment planning system determines a set of spots, typically to fulfil some criteria with respect to target coverage and healthy tissue sparing. The spots are then communicated to the ion beam treatment delivery system, which delivers the ion beam. The treatment planning system and the ion beam treatment delivery system are connected in a way that is known in the art per se.

When the delivery by the ion beam treatment delivery system needs to be modelled, a Bragg peak chamber is often used to measure delivery of a single spot in the form of an integrated depth dose (IDD). However, due to the limited lateral extent of the Bragg peak chamber, a fraction of the dose delivered by the single spot may be lost in the measurement, with the result that the measured IDD does not represent the complete IDD. If this discrepancy is not accounted for, the modelled delivery may significantly deviate from the total delivered dose. In the prior art, this discrepancy has been compensated for by adjusting the measured IDDs prior to using them in the beam modelling of the Treatment Planning System (TPS). These IDD adjustments are complex functions of depth and beam energy and are typically determined using some third-party Monte Carlo algorithm.

SUMMARY

One object is to improve modelling of delivery of ion beams.

According to a first aspect, it is provided a method for obtaining an energy spectrum of a focused ion beam, generated by an ion beam treatment delivery system, for a specific nominal energy, when a Bragg peak chamber is used to measure an integrated depth dose, IDD. The method is performed in a spectrum determiner and comprises the steps of: simulating doses, in at least two dimensions, of a set of nominally mono energetic focused ion beams, wherein the energies of the set cover a range of supported energies of the ion beam treatment delivery system; determining a lateral extension of a Bragg peak chamber to evaluate; calculating a set of theoretic component IDD curves, CIDDs, by laterally integrating the dose of the simulated set of the nominally mono energetic focused ion beams, over the lateral extension of the Bragg peak chamber; storing calculated CIDDs; obtaining a measured IDD of a focused ion beam with a nominal energy using the Bragg peak chamber; and performing a fit of a linear combination of CIDDs, wherein all CIDD weights are equal to, or greater than zero, to the measured IDD, to determine an energy spectrum for the focused ion beam with the nominal beam energy.

The energy distribution of each simulated nominally mono energetic focused ion beam may have an energy distribution with a standard deviation that is smaller than the standard deviation of the energy distribution of the focused ion beam of the treatment delivery system.

The energy distribution of each simulated nominally mono energetic focused ion beam may be strictly mono energetic.

The steps of obtaining a measured IDD and performing a fit may be repeated for a plurality of nominal beam energies. In this case, the method further comprises the step of: determining the energy spectrum for an additional nominal beam energy of the ion beam treatment delivery system by interpolation between previously determined energy spectra.

The method may further comprise the step of: using the energy spectrum as input to Monte Carlo based dose computation algorithms.

The method may further comprise the step of: generating a complete IDD using the energy spectrum and a second set of CIDDs that are laterally integrated over a larger area than that used to determine the CIDDs used for determining the energy spectra, the complete IDD being usable as input to analytical dose computation algorithms.

According to a second aspect, it is provided a spectrum determiner for obtaining an energy spectrum of a focused ion beam, generated by an ion beam treatment delivery system, for a specific nominal energy, when a Bragg peak chamber is used to measure an integrated depth dose, IDD. The spectrum determiner comprises: a processor; and a memory storing instructions that, when executed by the processor, cause the spectrum determiner to: simulate doses, in at least two dimensions, of a set of nominally mono energetic focused ion beams, wherein the energies of the set cover a range of supported energies of the ion beam treatment delivery system; determine a lateral extension of a Bragg peak chamber to evaluate; calculate a set of theoretic component IDD curves, CIDDs, by laterally integrating the dose of the simulated set of the nominally mono energetic focused ion beams, over the lateral extension of the Bragg peak chamber; store calculated CIDDs; obtain a measured IDD of a focused ion beam with a nominal energy using the Bragg peak chamber; and perform a fit of a linear combination of CIDDs, wherein all CIDD weights are equal to, or greater than zero, to the measured IDD, to determine an energy spectrum for the focused ion beam with the nominal beam energy.

The energy distribution of each simulated nominally mono energetic focused ion beam may have an energy distribution with a standard deviation that is smaller than the standard deviation of the energy distribution of the focused ion beam of the treatment delivery system The energy distribution of each simulated nominally mono energetic focused ion beam may be strictly mono energetic.

The spectrum determiner may further comprise instructions that, when executed by the processor, cause the spectrum determiner to: repeat the instructions to obtain a measured IDD and perform a fit for a plurality of nominal beam energies, and determine the energy spectrum for an additional nominal beam energy of the ion beam treatment delivery system by interpolation between previously determined energy spectra.

The spectrum determiner may further comprise instructions that, when executed by the processor, cause the spectrum determiner to: use the energy spectrum as input to Monte Carlo based dose computation algorithms.

The spectrum determiner may further comprise instructions that, when executed by the processor, cause the spectrum determiner to: generate a complete IDD using the energy spectrum and a second set of CIDDs that are laterally integrated over a larger area than that used to determine the CIDDs used for determining the energy spectra, the complete IDD being usable as input to analytical dose computation algorithms.

According to a third aspect, it is provided a computer program for obtaining an energy spectrum of a focused ion beam, generated by an ion beam treatment delivery system, for a specific nominal energy, when a Bragg peak chamber is used to measure an integrated depth dose, IDD. The computer program comprises computer program code which, when run on a spectrum determiner causes the spectrum determiner to: simulate doses, in at least two dimensions, of a set of nominally mono energetic focused ion beams, wherein the energies of the set cover a range of supported energies of the ion beam treatment delivery system; determine a lateral extension of a Bragg peak chamber to evaluate; calculate a set of theoretic component IDD curves, CIDDs, by laterally integrating the dose of the simulated set of the nominally mono energetic focused ion beams, over the lateral extension of the Bragg peak chamber; store calculated CIDDs; obtain a measured IDD of a focused ion beam with a nominal energy using the Bragg peak chamber; and perform a fit of a linear combination of CIDDs, wherein all CIDD weights are equal to, or greater than zero, to the measured IDD, to determine an energy spectrum for the focused ion beam with the nominal beam energy.

According to a fourth aspect, it is provided a computer program product comprising a computer program according to the third aspect and a computer readable means on which the computer program is stored.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

Aspects and embodiments are now described, by way of example, with reference to the accompanying drawings, in which.

DETAILED DESCRIPTION

The aspects of the present disclosure will now be described more fully hereinafter with reference to the accompanying drawings, in which certain embodiments of the invention are shown. These aspects may, however, be embodied in many different forms and should not be construed as limiting; rather, these embodiments are provided by way of example so that this disclosure will be thorough and complete, and to fully convey the scope of all aspects of invention to those skilled in the art. Like numbers refer to like elements throughout the description.

Figure 1:
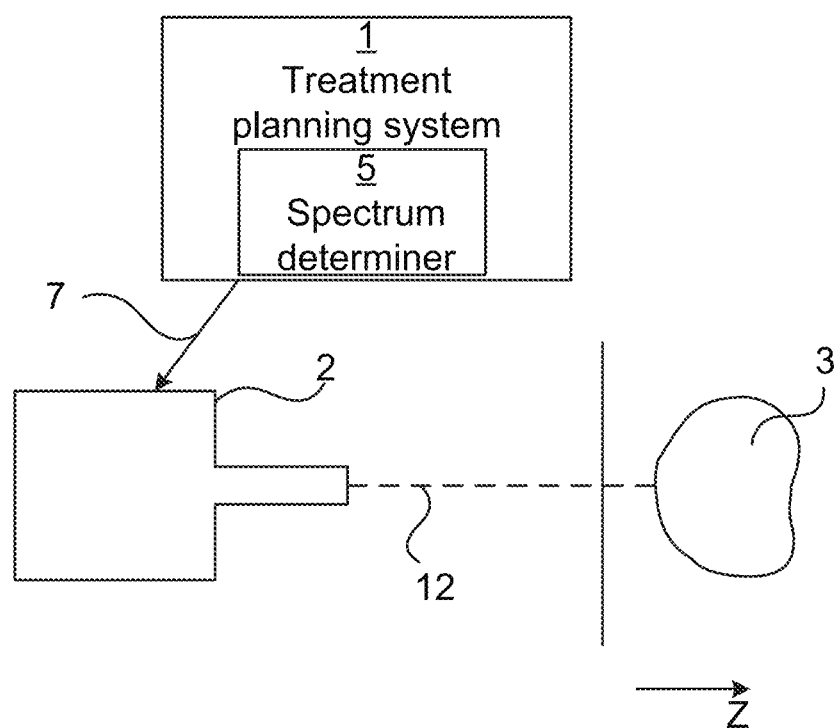
FIG. 1 is a schematic drawing illustrating an environment in which embodiments presented herein can be applied.

FIG. 1 is a schematic drawing illustrating an environment in which embodiments presented herein can be applied. A treatment planning system 1 determines how radiation doses are to be delivered to a target volume 3 of a patient. More specifically, the treatment planning system 1 supplies a treatment plan 7 to an ion beam treatment delivery system 2. The treatment plan 7 specifies weights for a plurality of geometrically defined scanning spots. Each weight defines an amount of radiation provided at the respective scanning spot, to thereby provide radiation dose to the target volume 3. There may be an organ at risk in proximity to the target volume 3. In that case, the treatment plan is determined with a balance between sufficient dose delivery to the target volume 3 while keeping dose delivery to the organ at risk low.

The treatment plan is delivered by the ion beam treatment delivery system 2 using a scanned ion beam, delivering dose to the patient in scanning spots. The scanning spot is defined by a lateral scan position for the beam and a beam energy. The treatment plan 7 is made up of a distribution of scanning spots for ion beam therapy, to thereby define dose delivery in three dimensions to the target volume 3.

Based on the treatment plan 7, the ion beam treatment delivery system 2 generates an ion beam 12 that is scanned spot by spot over the target volume 3 of a patient. Each scanning spot generates a spot dose distribution in the target volume 3 of the patient. In the coordinate system indicated in FIG. 1, depth is represented along a z axis. The location of the dose maximum (Bragg peak) of a spot dose distribution depth-wise, i.e. along the z axis, is controlled by the kinetic energy of the ions; higher energy results in a deeper location of the dose maximum. Moreover, the lateral position in two dimensions (in a plane perpendicular to the z axis), is controlled using electromagnets to deflect the beam 12. In this way, the ion beam treatment delivery system 2 delivers the scanning spots in three dimensions in accordance with the treatment plan 7.

Figure 2:
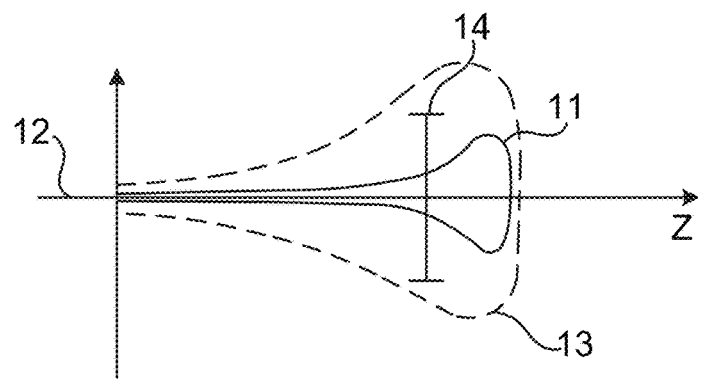
FIG. 2 is a schematic diagram illustrating lateral extension as a function of depth of the dose delivered by a single focused ion beam.

FIG. 2 is a schematic diagram illustrating lateral extension as a function of depth of the dose delivered by a single focused ion beam 11. Depth is indicated by the z axis and the vertical axis indicates a lateral direction. It can there be seen how a core dose delivery 11 (containing most of the dose delivery) of the ion beam 12 extends laterally from the centre of the ion beam 12, especially as it approaches the Bragg peak. A Bragg peak chamber is used to measure dose delivery in the form of integrated depth dose (IDD). The Bragg peak chamber to be any type of dosimetric device that is used to measure the IDD of a focused ion beam. The Bragg peak chamber has a finite lateral extension 14. While lateral extension 14 of the Bragg peak chamber covers the lateral extension of the core dose delivery 11, there is a small amount of dose that is delivered all the way to a peripheral dose delivery 13. Consequently, there will be some delivery of dose outside the finite lateral extension 14 of the Bragg peak chamber, which will thus not be captured by the Bragg peak chamber.

Figure 3:
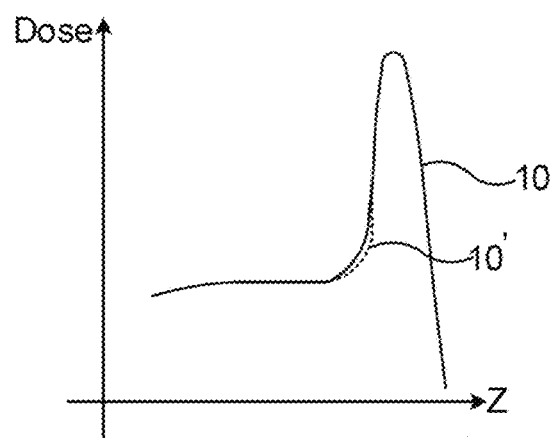
FIG. 3 is a schematic diagram illustrating the difference between total dose delivery and measured dose delivery, measured using a Bragg peak chamber with a finite lateral extension.

FIG. 3 is a schematic diagram illustrating the difference between total dose delivery 10 and measured dose delivery 10', measured using a Bragg peak chamber.

The total dose delivery 10 as well as the measured dose delivery 10' illustrate the presence of the Bragg peak at a specific depth and a sharp drop-off thereafter. Referring back to FIG. 2, due to the finite lateral extension 14 of the Bragg peak chamber, there will be small amounts of dose delivery which is not captured by the Bragg peak chamber. It is for this reason that there is a discrepancy between the measured dose delivery 10' and the total dose delivery 10. In the prior art, this discrepancy has been compensated for numerically.

Figure 4:
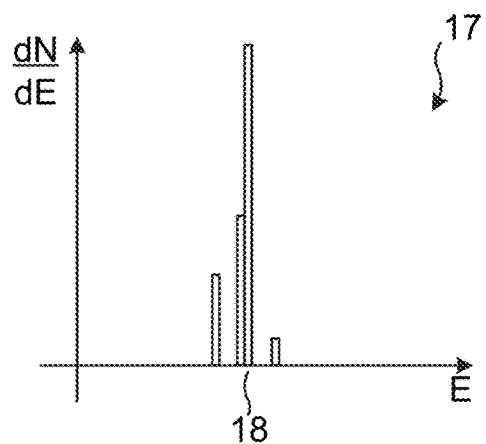
FIG. 4 is a schematic histogram illustrating the energy spectrum of a single ion beam in the ion beam treatment delivery system of FIG. 1.

FIG. 4 is a schematic histogram illustrating the energy spectrum of a single ion beam in the ion beam treatment delivery system 2 of FIG. 1. The single ion beam has a nominal energy, which is the configured energy in the ion beam treatment delivery system for this particular ion beam. Energy E is shown along the x axis and the y axis indicates distribution of energies in the ion beam, dN/dE. The energy intervals, i.e. the size of each bin for the energies, along the x axis can e.g. be 0.2 MeV. The ion beam has a certain nominal energy 18. However, as seen in the histogram, there is some variation in dose delivery for different energies around the nominal energy 18. In other words, in a real ion beam treatment delivery system, there is some variation in the energy level in ions of the ion beam, reflected by the energy spectrum 17 illustrated in FIG. 4.

Figure 5A:
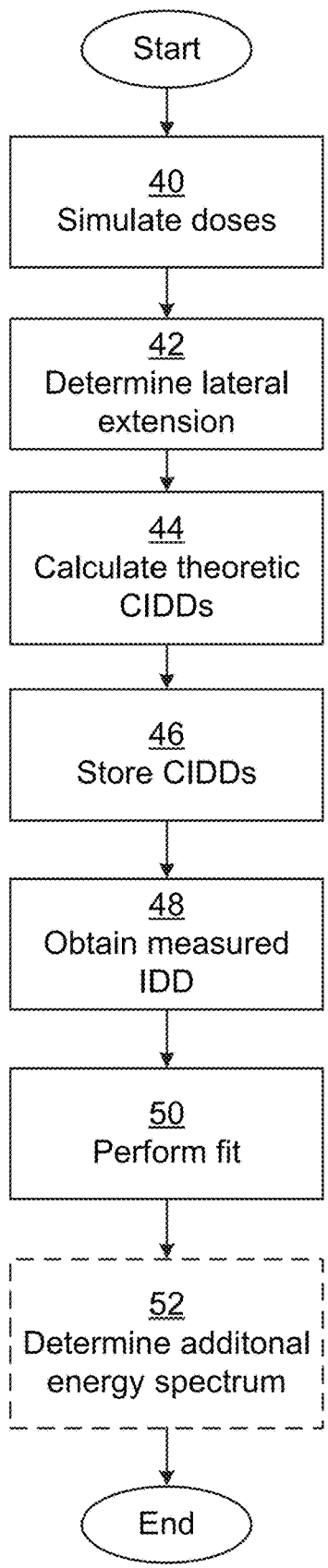
FIGS. 5A-C are flow charts illustrating methods for obtaining an energy spectrum of a focused ion beam.
Figure 5B:
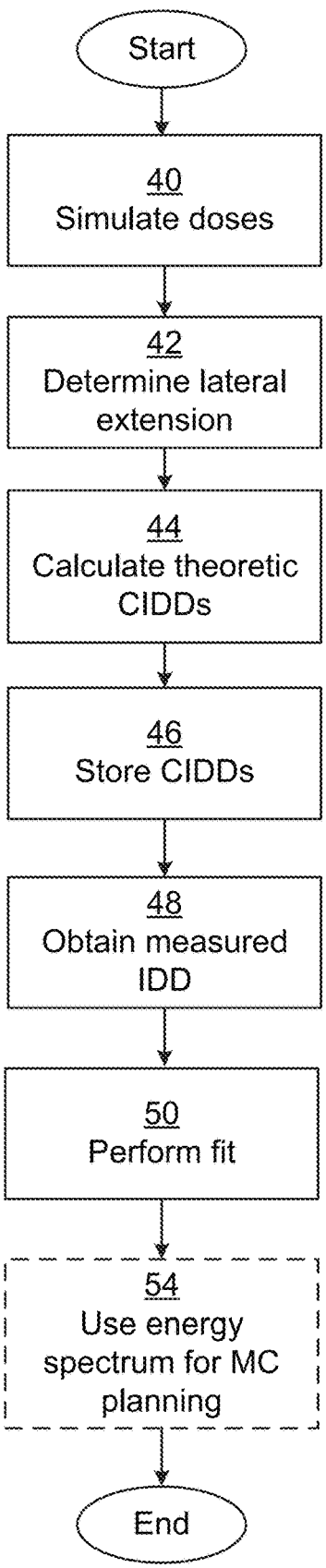
Figure 5C:
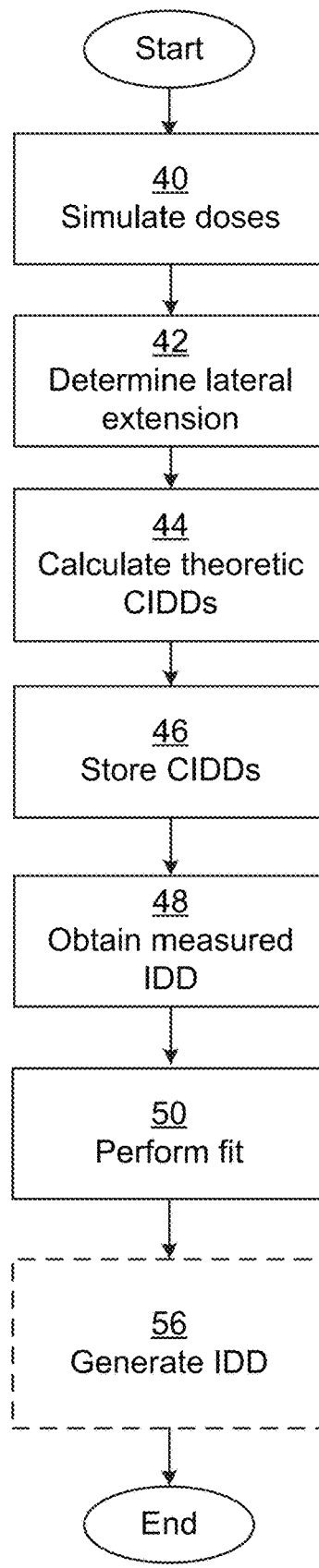

FIGS. 5A-C are flow charts illustrating methods for obtaining an energy spectrum of a focused ion beam. As explained above, the focused ion beam is generated by the ion beam treatment delivery system, for a specific nominal energy. A Bragg peak chamber is used to measure an integrated depth dose, IDD. The methods are performed in a spectrum determiner. First, embodiments illustrated by FIG. 5A will be described.

In a simulate doses step 40, the spectrum determiner simulates doses, in at least two dimensions (i.e. in two or three dimensions), of a set of nominally mono energetic focused ion beams. The energies of the set cover a range of supported energies of the ion beam treatment delivery system. As an example, the energies of the set cover between 5 MeV to 250 MeV. In one embodiment, the spacing between the simulated nominally mono energetic ion beams in the set is 0.2 MeV.

The energy distribution of each simulated nominally mono energetic focused ion beam does not need to be strictly mono energetic, as long as the energy distribution of the simulated ion beam is narrow compared to that of the ion beam treatment delivery system. For instance, the energy distribution of the mono energetic focused ion beams can have a standard deviation that is smaller than the standard deviation of the energy distribution of the focused ion beam of the treatment delivery system. In one embodiment, the energy distribution of each simulated nominally mono energetic focused ion beam is strictly mono energetic.

In a determine lateral extension step 42, the spectrum determiner determines a lateral extension of a Bragg peak chamber to evaluate. The lateral extension can be a diameter of a circular Bragg peak chamber or the area of the Bragg peak chamber.

In a calculate theoretic CIDDs step 44, the spectrum determiner calculates a set of theoretic component IDD curves, here denoted CIDDs. This calculation is performed by laterally integrating the dose of the simulated set of the nominally mono energetic focused ion beams, over the lateral extension of the Bragg peak chamber. In other words, the CIDDs are simulated measurements corresponding to in lateral extension to the size of the Bragg peak chamber.

In a store CIDDs step 46, the spectrum determiner stores the calculated CIDDs. The CIDDs can be precalculated and stored in advance, long before the measurement with the Bragg peak chamber occurs. Furthermore, CIDDs can be precalculated for several sizes of Bragg peak chambers, and only the CIDDs of the Bragg peak chamber used is later employed.

In an obtain measured IDD step 48, the spectrum determiner obtains a measured IDD of a focused ion beam with a nominal energy using the Bragg peak chamber.

In a perform fit step 50, the spectrum determiner performs a fit of a linear combination of CIDDs to the measured IDD (with the CIDDs corresponding in lateral extension to the Bragg peak chamber used in step 48). All CIDD weights are equal to, or greater than zero in this linear combination. In this way, an energy spectrum for the focused ion beam with the nominal beam energy is determined. The fit can e.g. be performed using a least squares method.

In one embodiment, steps 48 and 50 are repeated for a plurality of nominal beam energies. In this case, the method can further comprise an optional determine additional energy spectrum step 52.

In the optional determine additional energy spectrum step 52, the spectrum determiner determines the energy spectrum for an additional nominal beam energy of the ion beam treatment delivery system by interpolation between previously determined energy spectra.

Now, embodiments illustrated by FIG. 5B will be described. In the interest of clarity and brevity, only new or modified steps, compared to the embodiments of FIG. 5A will be described. It is to be noted that step 52 can optionally be performed in this embodiment also.

In a use energy spectrum for MC planning step 54, the spectrum determiner uses the energy spectrum as input to Monte Carlo based dose computation algorithms.

Now, embodiments illustrated by FIG. 5C will described. In the interest of clarity and brevity, only new or modified steps, compared to the embodiments of FIG. 5A will be described. It is to be noted that step 52 can optionally be performed in this embodiment also.

In a generate IDD step 56, the spectrum determiner generates a complete IDD (corresponding to the example shown in FIG. 3) using the energy spectrum and a second set of CIDDs that are laterally integrated over a larger area than that used to determine the CIDDs used for determining the energy spectra. The complete IDD is then usable as input to analytical dose computation algorithms.

Figure 6:
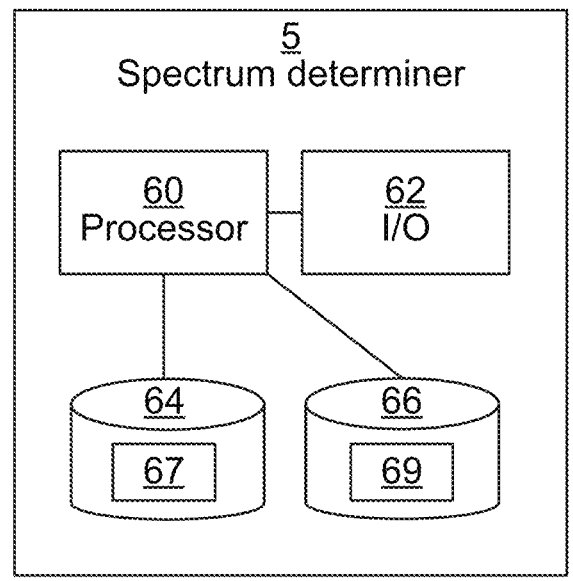
FIG. 6 is a schematic diagram illustrating components of the spectrum determiner of FIG. 1 according to one embodiment.

FIG. 6 is a schematic diagram illustrating components of the spectrum determiner 5 of FIG. 1 according to one embodiment. When the spectrum determiner 1 forms part of a host device, such as the treatment planning system 1 of FIG. 1, one or more of the mentioned components can be shared with the host device. A processor 60 is provided using any combination of one or more of a suitable central processing unit (CPU), multiprocessor, microcontroller, digital signal processor (DSP), application specific integrated circuit etc., capable of executing software instructions 67 stored in a memory 64, which can thus be a computer program product. The processor 60 can be configured to execute the method described with reference to FIGS. 5A-C above.

The memory 64 can be any combination of random-access memory (RAM) and read only memory (ROM). The memory 64 also comprises persistent storage, which, for example, can be any single one or combination of magnetic memory, optical memory, solid-state memory or even remotely mounted memory.

A data memory 66 is also provided for reading and/or storing data during execution of software instructions in the processor 60. The data memory 66 can be any combination of random-access memory (RAM) and read only memory (ROM).

The spectrum determiner 5 further comprises an I/O interface 62 for communicating with other external entities. Optionally, the I/O interface 62 also includes a user interface.

Other components of the spectrum determiner 5 are omitted in order not to obscure the concepts presented herein.

Figure 7:
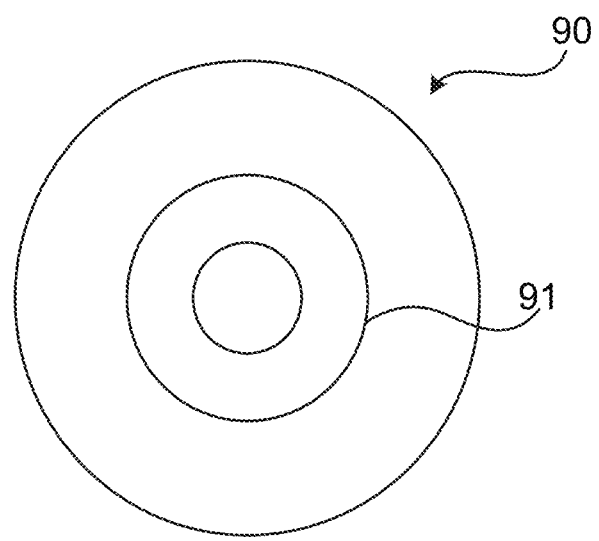
FIG. 7 shows one example of a computer program product comprising computer readable means.

FIG. 7 shows one example of a computer program product comprising computer readable means. On this computer readable means, a computer program 91 can be stored, which computer program can cause a processor to execute a method according to embodiments described herein. In this example, the computer program product is an optical disc, such as a CD (compact disc) or a DVD (digital versatile disc) or a Blu-Ray disc. As explained above, the computer program product could also be embodied in a memory of a device, such as the computer program product 64 of FIG. 6. While the computer program 91 is here schematically shown as a track on the depicted optical disk, the computer program can be stored in any way which is suitable for the computer program product, such as a removable solid-state memory, e.g. a Universal Serial Bus (USB) drive.

The aspects of the present disclosure have mainly been described above with reference to a few embodiments. However, as is readily appreciated by a person skilled in the art, other embodiments than the ones disclosed above are equally possible within the scope of the invention, as defined by the appended patent claims. Thus, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method for obtaining an energy spectrum of a focused ion beam, generated by an ion beam treatment delivery system, for a specific nominal energy, when a Bragg peak chamber is used to measure an integrated depth dose (IDD), the method being performed in a spectrum determiner and comprising the steps of:
    simulating doses, in at least two dimensions, of a set of nominally mono energetic focused ion beams, wherein the energies of the set cover a range of supported energies of the ion beam treatment delivery system;
    determining a lateral extension of a Bragg peak chamber to evaluate;
    calculating a set of theoretic component IDD curves (CIDDs) by laterally integrating the dose of the simulated set of the nominally mono energetic focused ion beams, over the lateral extension of the Bragg peak chamber;
    storing calculated CIDDs;
    obtaining a measured IDD of a focused ion beam with a nominal energy using the Bragg peak chamber; and
    performing a fit of a linear combination of CIDDs, wherein all CIDD weights are equal to or greater than zero, to the measured IDD, to determine an energy spectrum for the focused ion beam with the nominal beam energy.

2. The method according to claim 1, wherein the energy distribution of each simulated nominally mono energetic focused ion beam has an energy distribution with a standard deviation that is smaller than the standard deviation of the energy distribution of the focused ion beam of the treatment delivery system.

3. The method according to claim 1, wherein the energy distribution of each simulated nominally mono energetic focused ion beam is strictly mono energetic.

4. The method according to claim 1, wherein the steps of obtaining a measured IDD and performing a fit are repeated for a plurality of nominal beam energies, and wherein the method further comprises the step of:
    determining the energy spectrum for an additional nominal beam energy of the ion beam treatment delivery system by interpolation between previously determined energy spectra.

5. The method according to claim 1, further comprising the step of:
    using the energy spectrum as input to Monte Carlo based dose computation algorithms.

6. The method according to claim 1, further comprising the step of:
    generating a complete IDD using the energy spectrum and a second set of CIDDs that are laterally integrated over a larger area than that used to determine the CIDDs used for determining the energy spectra, the complete IDD being usable as input to analytical dose computation algorithms.

7. A spectrum determiner for obtaining an energy spectrum of a focused ion beam, generated by an ion beam treatment delivery system, for a specific nominal energy, when a Bragg peak chamber is used to measure an integrated depth dose (IDD), the spectrum determiner comprising:
    a processor; and
    a memory storing instructions that, when executed by the processor, cause the spectrum determiner to:
    simulate doses, in at least two dimensions, of a set of nominally mono energetic focused ion beams, wherein the energies of the set cover a range of supported energies of the ion beam treatment delivery system;
    determine a lateral extension of a Bragg peak chamber to evaluate;
    calculate a set of theoretic component IDD curves (CIDDs), by laterally integrating the dose of the simulated set of the nominally mono energetic focused ion beams, over the lateral extension of the Bragg peak chamber;

store calculated CIDDs;

obtain a measured IDD of a focused ion beam with a nominal energy using the Bragg peak chamber; and perform a fit of a linear combination of CIDDs, wherein all CIDD weights are equal to or greater than zero, to the measured IDD, to determine an energy spectrum for the focused ion beam with the nominal beam energy.

8. The spectrum determiner according to claim 7, wherein the energy distribution of each simulated nominally mono energetic focused ion beam has an energy distribution with a standard deviation that is smaller than the standard deviation of the energy distribution of the focused ion beam of the treatment delivery system.

9. The spectrum determiner according to claim 7, wherein the energy distribution of each simulated nominally mono energetic focused ion beam is strictly mono energetic.

10. The spectrum determiner according to claim 7, further comprising instructions that, when executed by the processor, cause the spectrum determiner to:

repeat the instructions to obtain a measured IDD and perform a fit for a plurality of nominal beam energies; and determine the energy spectrum for an additional nominal beam energy of the ion beam treatment delivery system by interpolation between previously determined energy spectra.

11. The spectrum determiner according to claim 7, further comprising instructions that, when executed by the processor, cause the spectrum determiner to:

use the energy spectrum as input to Monte Carlo based dose computation algorithms.

12. The spectrum determiner according to claim 7, further comprising instructions that, when executed by the processor, cause the spectrum determiner to:

generate a complete IDD using the energy spectrum and a second set of CIDDs that are laterally integrated over a larger area than that used to determine the CIDDs used for determining the energy spectra, the complete IDD being usable as input to analytical dose computation algorithms.

13. A computer program product comprising a non-transitory computer readable medium storing a computer program for obtaining an energy spectrum of a focused ion beam, generated by an ion beam treatment delivery system, for a specific nominal energy, when a Bragg peak chamber is used to measure an integrated depth dose (IDD), the computer program comprising computer program code which, when run on a spectrum determiner causes the spectrum determiner to:

simulate doses, in at least two dimensions, of a set of nominally mono energetic focused ion beams, wherein the energies of the set cover a range of supported energies of the ion beam treatment delivery system;

determine a lateral extension of a Bragg peak chamber to evaluate;

calculate a set of theoretic component IDD curves (CIDDs), by laterally integrating the dose of the simulated set of the nominally mono energetic focused ion beams, over the lateral extension of the Bragg peak chamber;

store calculated CIDDs;

obtain a measured IDD of a focused ion beam with a nominal energy using the Bragg peak chamber; and perform a fit of a linear combination of CIDDs, wherein all CIDD weights are equal to or greater than zero, to the measured IDD, to determine an energy spectrum for the focused ion beam with the nominal beam energy.

* * * * *